(12) United States Patent
Boucher et al.

(10) Patent No.: US 7,933,647 B2
(45) Date of Patent: Apr. 26, 2011

(54) METHODS OF INCREASING LIPOLYSIS

(75) Inventors: Jean P. Boucher, St-Constant (CA);
Roland Savard, Mont-St-Hilaire (CA);
Michel Portmann, Ste-Thérèse (CA);
Zied Haj Hamida, Montreal (CA)

(73) Assignee: Transfert Plus, S.E.C., Quebec (CA)

( * ) Notice: Subject to any disclaimer, the term of this patent is extended or adjusted under 35 U.S.C. 154(b) by 49 days.

(21) Appl. No.: 10/588,383

(22) PCT Filed: Jun. 7, 2006

(86) PCT No.: PCT/CA2006/000938
§ 371 (c)(1),
(2), (4) Date: Nov. 29, 2006

(87) PCT Pub. No.: WO2006/130979
PCT Pub. Date: Dec. 14, 2006

(65) Prior Publication Data
US 2008/0145906 A1 Jun. 19, 2008

Related U.S. Application Data

(60) Provisional application No. 60/687,872, filed on Jun. 7, 2005.

(51) Int. Cl.
*A61N 1/00* (2006.01)
(52) U.S. Cl. ............... 604/20; 435/173.1; 435/173.4
(58) Field of Classification Search ............... 435/173.1, 435/173.4
See application file for complete search history.

(56) References Cited

U.S. PATENT DOCUMENTS

| | | | | |
|---|---|---|---|---|
| 4,016,886 | A * | 4/1977 | Doss et al. | 607/99 |
| 5,425,752 | A | 6/1995 | Vu'Nguyen | |
| 5,507,790 | A * | 4/1996 | Weiss | 607/100 |
| 5,782,826 | A * | 7/1998 | Swanson | 606/34 |
| 5,810,762 | A | 9/1998 | Hofmann | |
| 5,913,836 | A | 6/1999 | Groux | |
| 6,326,177 | B1 | 12/2001 | Schoenbach et al. | |
| 6,492,130 | B1 | 12/2002 | Wilkison et al. | |
| 6,697,670 | B2 | 2/2004 | Chomenky et al. | |
| 2002/0138117 | A1 | 9/2002 | Son | |
| 2002/0193831 | A1 | 12/2002 | Smith | |
| 2003/0236487 | A1 | 12/2003 | Knowlton | |
| 2004/0210214 | A1 | 10/2004 | Knowlton | |

FOREIGN PATENT DOCUMENTS

| | | |
|---|---|---|
| SU | 1805983 A3 * | 3/1993 |
| WO | WO/95/29732 | 11/1995 |

OTHER PUBLICATIONS

Chan, TM et al. Activation of lipolysis by epinephrine and electrical stimulation in the perfused hindquarters of lean and obese-diabetic (db/db) mice. Biochimica et Biophysica Acta. 1983. 751: 384-392.*
Kumon, A et al. Mechanism of lipolysis induced by electrical stimulation of the hypothalamus in the rabbit. Journal of Lipid Research. 1976. 17: 551-558.*
English Translation of SU 1805983 A3 (publication date of Russian document: Mar. 1993).*
Bruggemann, A. et al., Nature, 1993, vol. 365, pp. 445-448.
Chung, S., et al, The Journal of Neuroscience, 1995, vol. 15, pp. 3927-3935.
Deadwyler, S. et al., J. Pharmacol Exp Ther., 1995, vol. 273, pp. 734-743.
Ramirez-Ponce, M.P., et al., J. Membrane Biol., 2003, vol. 196, pp. 129-134.
Ramirez-Ponce, M.P., et al., Biochemical and Biophysical Research Communications, 1996, vol. 223, pp. 250-256.
Ramirez-Ponce, M.P. et al., Revista Espanola de Fisiologia, 1990, vol. 46, No. 2, pp. 133-138.
Ramirez-Ponce, M.P. et al., Revista Espanola de Fisiologia, 1991, vol. 47, No. 4, pp. 217-221.
Ramirez-Ponce, M.P. et al., Journal of Endocrinology, 1998, vol. 159, pp. 397-402.
Wilson, S., et al., Am J. Physiol Cell Physiol, 2000, vol. 279, C1847-C1858.

* cited by examiner

*Primary Examiner* — Allison M. Ford
*Assistant Examiner* — Susan E. Fernandez
(74) *Attorney, Agent, or Firm* — Birch, Stewart, Kolasch & Birch, LLP

(57) ABSTRACT

Methods for increasing lipolysis in a cell are described herein. Such methods comprise the application of an electrical current to a cell. In an embodiment, the application of the electrical current does not substantially alter the viability of such cell and/or preserves the viability of such cell. In an embodiment, such cell is an adipocyte. Corresponding uses and packages are also described.

15 Claims, 6 Drawing Sheets

METHODS OF INCREASING LIPOLYSIS

This National Phase application claims priority under 35 U.S.C. 119(e) to U.S. Provisional Application No. 60/687,872 filed on Jun. 7, 2005. This application is hereby expressly incorporated by reference into the present application.

TECHNICAL FIELD

The present application relates to methods for increasing lipolysis in cells, especially adipocyte-associated lipolysis. Such methods may comprise the application of an electrical current to the cells. The application of such current increases lipolysis in the cells while substantially preserving the cells' viability.

BACKGROUND OF THE INVENTION

Women, as well as an increasing number of men, are obsessed by the way they look and seek new alternatives to improve their body image. Although effective, surgical removal of fat is costly and may also be risky. As such, various less intrusive methods have been designed and are used to reduce the amount and appearance of fat.

One of these methods is electrolipolysis, wherein electrical stimulation is said to cause the reduction in the amount or the appearance of fat. Such technology is described in various publications (such as U.S. Pat. Nos. 5,913,836 (issued Jun. 22, 1999), 5,425,752 (issued Jun. 20, 1995), 5,810,762 (issued Sep. 22, 1998), 6,326,177 (issued Dec. 4, 2001), 6,697,670 (issued Feb. 4, 2004), U.S. patent applications Nos. 2002/0138117 (published Sep. 26, 2002), 2002/0193831 (published Dec. 19, 2002) and International patent application publication No WO/1995/029732 (published Nov. 9, 1995)). These techniques usually involve the reduction of the number of adipocytes, mostly by inducing cellular death which may produce an inflammatory response and, in the long term, increase the number of adipose cell as a direct rebound reaction.

Another class of methods for reducing the appearance of fat consists in modulating the activity of specific receptors on lipid containing cells to activate lipolysis in these cells, by either decreasing liponeogenesis or increasing lipolysis. One receptor implicated in mediating liponeogenic/lipolytic effects is the sulfonylurea-1 receptor (SUR 1). This receptor, described in U.S. Pat. No. 6,492,130 (issued Dec. 10, 2002), is expressed by adipocytes, and activates potassium channels.

Another receptor implicated in lipolysis is the β-adrenergic receptor. β-adrenergic receptors coupled signaling pathways are stimulated by natural hormones, such as noradrenalin and adrenalin. Upon activation of these receptors, the $α_S$ subunit of the $G_S$ protein normally coupled to the receptors, dissociates and activates the membrane-bound adenylate cyclase, which transforms ATP into cyclic AMP (cAMP). Consequently, intracellular cAMP builds up and activates the protein kinase A (PKA). PKA then phosphorylates and activates the hormone-sensitive lipase which rapidly leads to the activation of a lipolytic cascade and to the liberation of free fatty acids and glycerol.

β-adrenergic receptors associated signal transduction pathways are rapidly activated upon stimulation and induce drastic intracellular modifications. The activity of these receptors is thus tightly regulated. Thirty minutes following their activation, the β-adrenergic receptors are phosphorylated by various cellular kinases (such as PKA, protein kinase C or PKC, and the β adrenergic receptor kinase or β-ARK) which decrease the receptors' activity and ultimately leads, two hours later, to the desensitization (e.g. unresponsiveness) of the receptors. In addition, when the receptors are stimulated over a long period of time, the receptors are internalized and degraded, which ultimately reduces the total number of receptors and further enhances the desensitization phenomenon. As such, these β-adrenergic receptors are no longer able to stimulate lipolysis in adipocytes ("desensitization" phenomena).

This "desensitization" phenomenon is frequently observed in obese subjects or in subjects having excessive android or gynoid fat deposition. Consequently, in these subjects, the stimulation of the β-adrenergic receptors does not lead to lipolysis and fat reduction.

It would be highly desirable to be provided with methods for increasing lipolysis in a subject. In an embodiment, such methods should not involve the β-adrenergic receptor or its associated signaling pathways and/or cause the desensitization of such receptors. In another embodiment, such methods should limit cell death and/or preserve cell viability.

SUMMARY OF THE INVENTION

In accordance with the present invention, there is provided a method for increasing lipolysis in a cell of a subject, said method comprising applying an electrical current to said cell, wherein said cell remains substantially viable following said application.

Still in accordance with the present invention, there is provided the use of an electrical current to increase lipolysis in a cell, wherein said electrical current substantially preserving the viability of said cell.

Further in accordance with the present invention, there is provided a package comprising: means for applying an electrical current; and instructions for using said means in increasing lipolysis in a cell; wherein said electrical current substantially preserves the viability of said cell.

In another embodiment of the present invention, said electrical current is biphasic or monophasic.

In accordance with the present invention said electrical current at cell level is from about 2 mA to about 6 mA, more preferably is about 4 mA.

In another embodiment, said electrical current causes a depolarization of the membrane of said cell. In addition, the depolarization causes an alteration in the activity of an ion channel in said cell.

In accordance with the present invention, said depolarization causes a decrease in the activity of an ion channel in said cell. The ion channel is preferably one from the ion channel family selected from the group consisting of EAG, KCNQ, SK, slo, and Kv.

In addition, the ion channel is selected from the group consisting of eag, erg, elk, KCNQ1, KCNQ2, KCNQ3, KCNQ4, KCNQ5, Kv1, Kv2, Kv3, Kv4, Kv5, Kv6, Kv7, Kv8, and Kv9.

In addition, the ion channel is a potassium channel

In another embodiment of the present invention, said cell is an adipocyte.

In a further embodiment, the subject is a mammal, more preferably a human.

In accordance with the present invention, the adipocyte is located in a subcutaneous tissue, a visceral adipose tissue or an intramuscular tissue. Further, the subcutaneous tissue is located in a region selected from the group consisting of arm, knee, calf, abdomen, thigh, buttock and hip.

In accordance with the present invention, the increase in lipolysis is at least 1.5 fold with respect to the level of lipolysis in a control cell.

In accordance with the present invention, it is disclosed a use of the present invention for treating associated disorder with fat distribution. More preferably, the associated disorder with fat distribution is selected from the group consisting of lipodystrophy and obesity.

In another embodiment, the use of the present invention is further associated with another treatment selected in the group consisting of an exercise regime, a diet, aesthetic/cosmetic means and electrolyte drinks.

DETAILED DESCRIPTION OF THE PREFERRED EMBODIMENT

Figure 1:
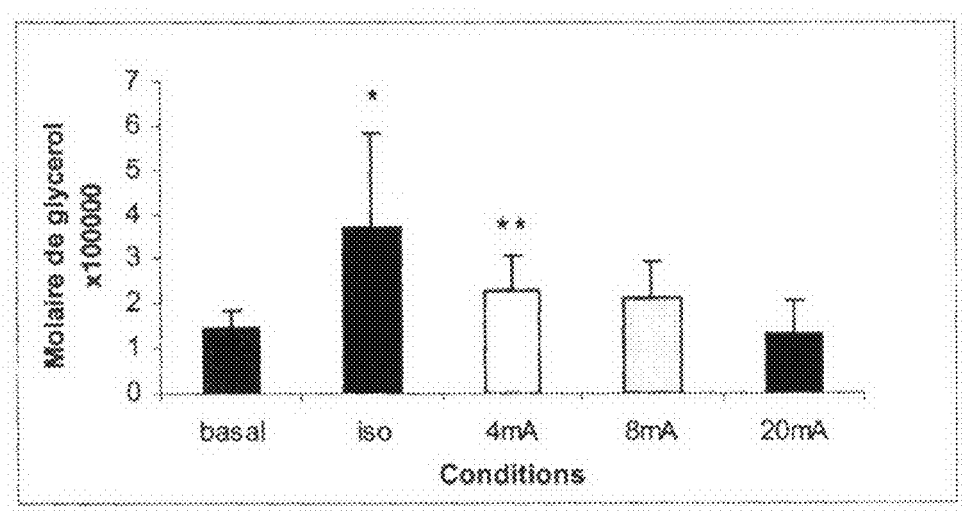
FIG. 1 illustrates a histogram of the means and standard deviations for the various conditions tested, wherein the results are expressed as $10^5$ M of released glycerol.

In accordance with the present invention, there is provided methods, uses, and packages for increasing lipolysis. Such methods, uses, and packages comprise the application of an electrical current and substantially preserve the viability.

In a first aspect, the present invention provides a method of increasing lipolysis in a cell. The term "lipolysis" is intended to mean the hydrolysis of lipids. More specifically, the term fat cell "lipolysis" is also used to encompass the hydrolysis of intracellular triglycerides and the release of free fatty acids and glycerol from cells. Lipolysis usually takes place intracellularly in cells containing a lipid droplet. Lipolysis can be measured by various ways to those skilled in the art, such as the assessment of free fatty acids release and of glycerol release (refer to the Examples below), by bioluminescence, etc. The assessment of glycerol release from cells is a better manner to measure lipolysis since glycerol cannot reenter fat cells when released while free fatty acids can.

The method comprises applying an electrical current to the cell. In an embodiment, the said cell remains substantially viable following the application of the current. As used herein, the term "viable" or "viability" is intended to mean the capacity of a cell to perform its intended functions. The cell's functions may vary according to the type of cell. Cellular functions may include, for example, cellular division, translation, transcription, protein assembly and maturation, protein secretion, storage of compounds (e.g. proteins, lipids, etc.), responsiveness to external stimuli, migration, etc. A method wherein a cell remains "substantially viable" following the application of the electrical current is one that does not irreversibly alter the cell's ability to perform its intended function. Alternatively, when applied to a population of cells, such method does not induce cell death (either by apoptosis or lysis) in a majority of cells, nor does it cause an alteration in the functions of a majority of cells. In an embodiment, the application of the electrical current preserves the viability of more than 50% of the cells, more than 60% of the cells, more than 70% of the cells, more than 80% of the cells, more than 90% of the cells, more than 95% of the cells, or more than 99% of the cells. In the present invention, the viability of fat cells refers to their ability to activate lipolysis by β-adrenergic receptors and by non-significant amount of cell lysis.

As mentioned above, the electrical current should be suitable for administration or application at the physiological level. Electrical current can be measured in amperes (A) or milliamperes (mA). The intensity of the electrical current can be measured in different ways using various means known by those skilled in the art. In an embodiment, the intensity of the electrical current is measured using an ammeter (refer to the Examples above), or with an oscilloscope. In an embodiment, the electrical current applied is less than 8 mA, and, in a further embodiment, less than 7 mA. For example, the electrical current may be from about 2 mA to about 6 mA. In yet a further embodiment, the electrical current may be 4 mA. The above electric current is one "felt" at the level of the cell. One skilled in the art will have to adjust this value as a function of the subject to be treated, the percentage of fat and/or muscle of the area to be treated in a subject. This value will also vary according to the impedance of the skin. One skilled person of the art will readily know how to measure the electric current "felt" at the level of the cell, i.e. the current that reach the cell and to which the cell is subjected.

In an embodiment, the electrical current applied may depolarize the membrane of the cell. Living cells maintain a difference in the concentrations of ions (e.g. cations) across their cellular membrane. This difference in ion distribution on either side of the cell membrane enables the formation a difference of potential across the cell membrane (e.g. the membrane potential). Usually, in resting cells, the intracellular space contains more negative electrolytes (e.g. anions) or less positive ions (cations) than the extracellular milieu. In the methods described herein, the application of the electrical current may alter (e.g. lower) the difference of potential between either side of the cell membrane and consequently alter (e.g. lower) the membrane potential.

The voltage or membrane potential arises from differences in concentration of the electrolytes (e.g. ions) across the cell membrane. In order to achieve this difference in ionic concentration, these cells usually contain ion channels and ion pumps. The term "ion channel" is intended to mean a membrane-spanning polypeptide capable of controlling the movement of certain ions across the membrane. Such channel enables the formation of an ion gradient on either side of the cellular membrane and, consequently, enables the polarization of the cell membrane. In another embodiment, the depolarization caused by the electrical current may alter (e.g. decrease) the activity of such ion channel in the cell.

In some cells, it is the difference in the concentration of potassium (K+) and sodium (Na+) electrolytes (or ions) that enables the formation of a membrane potential. As such, in an embodiment, the ion channel described above is a potassium channel. In yet a further embodiment, the potassium channel may comprise one of the polypeptidic sequences. In a more general manner, in the present invention the electric current can interfere with ion channels to either open such channel or close same to create a membrane potential arising from differences in concentration of the electrolytes (e.g. ions) across the cell membrane. The ion channels that can be affected in the present invention are for example, but without limitation, those from the EAG (eag, erg, and elk), KCNQ (KCNQ1, KCNQ2, KCNQ3, KCNQ4, and KCNQ5), SK, slo, and Kv (Kv1, Kv2, Kv3, Kv4, Kv5, Kv6, Kv7, Kv8, and Kv9) families. All of these ion channel families, and their specific members, are known to those skilled in the art.

Ramirez-Ponce et al. have demonstrated the presence of voltage-gated potassium channels in rat (1990, "Electrical activity in white adipose tissue of rat", Rev. Esp. Fisiol. 46(2): 133-188; 1991, "Effects of noradrenaline and insulin on electrical activity in white adipose tissue of rat", Rev. Esp. Fisiol. 47: 217-21; 1996, "Voltage-Dependent Potassium Channels in White Adipocytes", Biochemic and Biophysical Research Communications; and 1998, "Noradrenaline modulates the electrical activity of white adipocytes by a cAMP-dependent mechanism", J Endocrinol) and human (2003, "Human Adipose Cells Have Voltage-dependent Potassium Currents", J. Membrane Biol. 196: 129-134) white adipocyte membranes. They have shown that lipolytic (e.g. noradrenaline) and non-lipolytic (e.g. insulin) hormones modulate the electrical properties of white adipocyte membranes. More specifically, they have shown that noradrenaline causes a depolarization of the adipocyte membrane, whereas insulin causes a hyperpolarization. They have suggested that, when adipocytes are stimulated with noradrenaline, the resulting accumulation of intracellular cAMP modulates (e.g. blocks) the potassium channels' conductance. The effect of cAMP on voltage-gated potassium channels has also been investigated in other cell types (Bruggmann et al. 1993, "Ether-a-go-go encodes a voltage-gated channel permeable to $K^+$ and $Ca^{2+}$ and modulated by cAMP", Nature 365: 445-448; Chung and Kaczmare 1995, "Modulation of the inactivation of voltage-dependent potassium channels by cAMP", J. Neurosci. 15: 3927-3935; Deadwyler et al. 1995, "Cannabinoids modulate voltage sensitive potassium A-current in hippocAMPal neurons via a cAMP-dependent process", Pharmacol. Exp. Ther. 273(2): 734-743; Wilson et al. 2000, "ATP and beta adrenergic stimulation enhance voltage-gated K current inactivation in brown adipocytes", Am. J. Physiol. 279: C1847-C1858).

Various cells may be used in the methods described above. Such cells include, but are not limited to, adipocytes. The term "adipocyte" is intended to mean a cell whose most known function is the storage and breakdown of fat. Adipocytes usually stain positively with Oil-Red-O (which shows the intracellular accumulation of lipids) and express the lipoprotein lipase as well as the glycerol 3-phosphate dehydrogenase. There are two types of adipocytes: white and brown adipocytes. White adipocytes contain mostly one large lipid droplet, whereas brown adipocytes contain mostly several small lipid droplets and many mitochondria. The cellular function of brown adipocytes is the production of thermal energy. Unless specified otherwise, and as used herein, the term "adipocyte" is used to denote white adipocytes.

In yet a further embodiment, the adipocyte may be located in various tissues. The methods can be applied in every location where adipocytes are present. The adipocytes may be located on the arm (e.g. lateral or posterior face), the abdomen (e.g. above and below the navel), on the hips, on the thigh (e.g. external, posterior or internal face), around the knee area (e.g. above the knee area, internal face), the calves (e.g. posterior face), the buttock.

The methods described herein can be used in adipose tissue that can be submitted to an electrical current. Such tissues include, but are not limited to, subcutaneous adipose tissues, visceral adipose tissues, and intramuscular tissues.

The methods described herein can be used to increase lipolysis in a cell by at least 1.5 fold with respect to a control cell. The control cell, as described herein, is a cell that has not been submitted to the electrical current, such as the control cell described in the Examples below. The control cell has not been submitted to any treatments that alters its lipolytic level. The control cell may be derived from the same subject as the cell submitted to the electrical current.

In another embodiment, the methods described herein may be used to remove fat in very specific areas, e.g. in tissues containing an amount of fat that may be removed for either aesthetic/cosmetic or therapeutic reasons. Fat deposition in men is usually observed in the abdominal region (e.g. android fat) whereas in women, it is usually observed in the hip, thigh and buttock regions (e.g. gynoid fat). Android fat is usually associated with a higher risk of cardiovascular complications. Although android fat is generally seen in men and gynoid fat in women, fat deposition pattern is not solely determined by sex. Some women, for example during or after menopause, will shift from a gynoid fat deposition pattern to an android fat deposition pattern. The methods described herein can also serve in the treatment of other disorders associated with fat distribution, such as lipodystrophy and obesity. The methods described herein can be used to accelerate the return to a normal fat condition following one or many pregnancies, to stop or slow down the anti-lipolytic effect of insulin in subject suffering from type II diabetes, or to favour the use of lipids during a training session.

The methods described herein can be used alone or in combination with other known techniques to increase lipolysis. For example, the methods can be used in combination with drugs known to induce lipolysis, such as β adrenergic receptor agonists, or other drugs such as methylxanthines (caffeine or theophyline) or estrogenic supplements. The methods could also be used in association with an exercise regime aimed at lowering the percentage of fat. Such exercise regime may include, but is not limited to, cardiovascular training and weight training (e.g. to build muscle mass and/or improve muscle endurance). The methods could also be used in association with a diet aimed at lowering the percentage of fat and/or overall weight (e.g. a low-carbohydrate diet, a low fat diet). The methods could also be used in association with other aesthetic/cosmetic means aimed at reducing the appearance of fat (e.g. anti-cellulite cream, lymphatic drainage, etc.). The methods could be further used in association with electrolyte drinks (such as Gatoraid™, Ultimate replenisher™, etc.) that would modify the electrolyte content of a tissue, thus modulating the effect of the methods of the present invention. The methods of the present invention could also be followed with an exercise program that a patient would adhere to for improving the metabolism getting rid of the fat so released by the method of the present invention.

The electrical current described herein can also be used for increasing lipolysis in a cell. Different embodiments of the electrical current have been described above. The electrical current used herein may also preserve the viability of a cell. The electrical current can be applied, for example, on adipocytes or on areas containing adipose tissues (different embodiments of the adipocytes and of the adipose tissues have been described above). The electrical current may also be suitable to be applied to a mammal, and further to a human.

The present invention also comprises packages comprising means for applying the electrical current and instructions for its use in increasing lipolysis. Different embodiments of the electrical currents and the uses have been described above.

The present invention will be more readily understood by referring to the following examples which are given to illustrate the invention rather than to limit its scope.

EXAMPLE I

Adipocyte Preparation for Lipolysis Stimulation and Measurement

Material and Methods

Tissue samples. Adipose tissues were obtained from 11 pre-menopaused women, aged under 45, who were undergoing liposuction or an aesthetic surgery in the supra-iliac region.

Adipocyte isolation. The adipose tissues were first placed in Krebs buffer and transported to the laboratory. Fragments of fresh adipose tissue were then incubated in a collagenase type II solution (reconstituted in Krebs buffer, 5 mg of collagenase per gm of tissue; Sigma) for 30 minutes at 37° C. under agitation (100 rpm) in a controlled atmosphere (95% $O_2$, 5% $CO_2$) (Rodbell, 1964). After the incubation period, the cellular suspension was filtered through a 250 μm nylon mesh and separated from the stromal and vascular fraction by flotation. The recuperated adipocytes were then washed three times with 5 mL of Krebs buffer (preheated at 37° C., without collagenase) to remove any trace of the collagenase. For the last wash, the concentration of adipocytes was adjusted to 500 cells/50 μL. Adipocytes were counted using a Neubauer hemacytometer using trypan blue dye. Only adipocytes containing a defined lipid droplet were considered for the purposes of the examples presented herein. The cell concentration was then adjusted between 500 and 1000 adipocytes/50 μL. The adipocyte isolation technique described herein enables the study of the cell structure, cellular ion, and nutriment transfer and the hormonal regulation of lipolysis.

Electrical stimulation. The cell suspension was placed between two carbon rubber electrodes. The electrodes are 4.7 cm wide and 1.4 cm large. They were placed 8 cm apart in a Petri dish. The electrodes were designed such that, when the Petri dish is closed, they contact the bottom of the dish.

A power generator (such as K0406, 0-30 Vdc, 50 mA, or Grass S80 adapted to follow in real-time the variation of current and impedance, so as to be able to preferably maintain the current constant at the level of the cell) was used to tightly control the current. In all the experimentations performed, square waves impulses lasting 500 ms followed by a non-stimulatory period of 500 ms (corresponding to a frequency of 1 Hz) were used. The current intensity was either 4, 8 or 20 mA. Current intensity was closely monitored with an ammeter (such as FLUKE 179) on the anode side. Impulses were monitored with an oscilloscope (Tektronix™ TDS 2022, Digital storage oscilloscope, USA).

Cells were electrically stimulated for 30 minutes in an agitated water bath (40 rpm) at 37° C. Cells not submitted to the electrical current were either used as control cells (e.g. BASAL) or stimulated with isoproterenol (SIGMA: ISO, $10^{-4}$ M).

Resistance along an electrode somehow varies between 30 and 60 ohms. The resistance of the solution is estimated to about 10 ohms. This difference in resistances enables the formation of an electrical field that covers the entire surface of the Petri dish. Because the solution's resistance is lower than the electrode's resistance and because the solution is shaken during the entire stimulation period, the adipocytes are thought to be uniformly stimulated.

Evaluation of lipolysis. Because free fatty acids can be re-esterified Inside the adipocyte while glycerol is not, lipolysis was evaluated by measuring the release of glycerol. Glycerol was indirectly measured by assessing the formation of NADH produced during its enzymatic transformation. NADH was measured using a spectrophotometer (Pharmacia LKB-Novaspec), at a wavelength of 340 nm. Results are expressed as μmol of glycerol released per $10^6$ adipocytes per 30 minutes.

Evaluation of cell viability. Cell viability was assessed by counting viable cell using a Neubauer hematocytometer and the trypan blue dye. Cell viability was assessed before electrical stimulation (0 min.) and after electrical stimulation (30 min., 60 min. or 90 min.).

Statistical analysis. Experiments were performed in triplicates. Cells obtained from eleven (11) individuals were used for the control (BASAL), isoproterenol stimulation (ISO) and 4 mA conditions. Cells from four (4) individuals were used for the 8 mA condition and from seven (7) individuals for the 20 mA condition. The mean and standard deviation were calculated.

EXAMPLE II

Adipocyte Lipolysis Obtained Following Electrical Stimulation

Results

Adipocytes were isolated and electrically stimulated as described in Example 1. Table 1 summarize the results obtained.

Table 1

Statistical Analysis of the Obtained (μM of glycerol)

TABLE 1

Statistical analysis of the data obtained (μM of glycerol)

| Experimental condition | BASAL | ISO | 4 mA | 8 mA | 20 mA |
|---|---|---|---|---|---|
| Mean | 1.4 | 3.7 | 2.3 | 2.1 | 1.4 |
| Standard deviation | 0.4 | 2.1 | 0.8 | 0.9 | 0.7 |
| Coefficient of variation | 29% | 57% | 34% | 41% | 53% |
| N | 11 | 11 | 11 | 4 | 7 |

Results presented herein show that adipocyte lipolysis was increased 2.6 fold when adipocytes were stimulated with isoproterenol compared to control values (BASAL, e.g. no treatment). At a concentration of $10^{-4}$ M, isoproterenol is known to stimulate β-adrenergic receptors, stimulate lipolysis and facilitate glycerol release.

As shown on FIG. 1, an electrical stimulation with a 4 mA current increased adipocyte lipolysis 1.6 folds above basal values (p<0.001). Lipolysis measured for the isoproterenol (ISO) condition is significantly higher than the lipolysis measured for the control (BASAL) condition. Lipolysis measured for the 4 mA condition is significantly higher than the lipolysis measured for the control (BASAL) condition, but is not significantly different from the lipolysis measured for the isoproterenol (ISO) condition. The stimulation of lipolysis induced by the 4 mA current is not statistically different from the one induced by isoproterenol administration.

EXAMPLE III

Adipocyte Lipolysis Obtained Following Biphasic Electrical Stimulation

It was tested if biphasic electrical stimulation can induce lipolysis in adipocyte.

4 women between 40-52 years of age were used as subject. Adipose tissue was obtained from suprailiac areas through liposuction.

Figure 2:
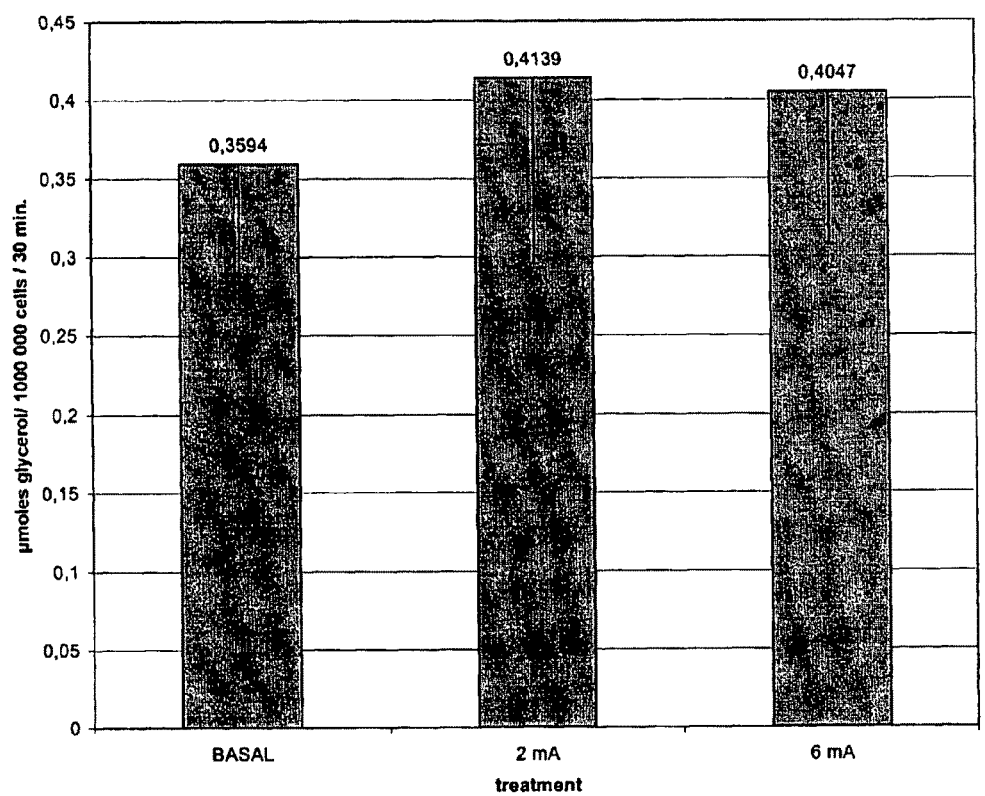
FIG. 2 illustrates the effect of biphasic electrical stimulation on adipocyte lipolysis in humans.

It is disclosed that isoproterenol (ISO) increased adipocyte lipolysis by 15% i.e. at a non significant level (FIG. 2). This data is very important since it clearly shows that the 4 women are resistant to loose fat through the β-adrenergic receptor stimulation, which is known as the main pathway of adipocyte lipolysis stimulation. On the other hand, the 6 mA biphasic stimulation significantly (through repeated T test procedures) increased lipolysis by 2.3 fold over basal thus counteracting the adipocyte β-adrenergic resistance observed with ISO. Moreover, the 4 mA biphasic stimulation increased basal lipolysis by 1.8 x thus at a lower level than the 6 mA stimulation.

These data confirm that a biphasic electrical stimulation can successfully yield to losses of fat in adipose tissue.

EXAMPLE IV

Adipocyte Lipolysis Obtained Following Monophasic Electrical Stimulation

In correlation with the present invention, monophasic stimulation on adipocyte lipolysis in humans was also measured.

Figure 3:
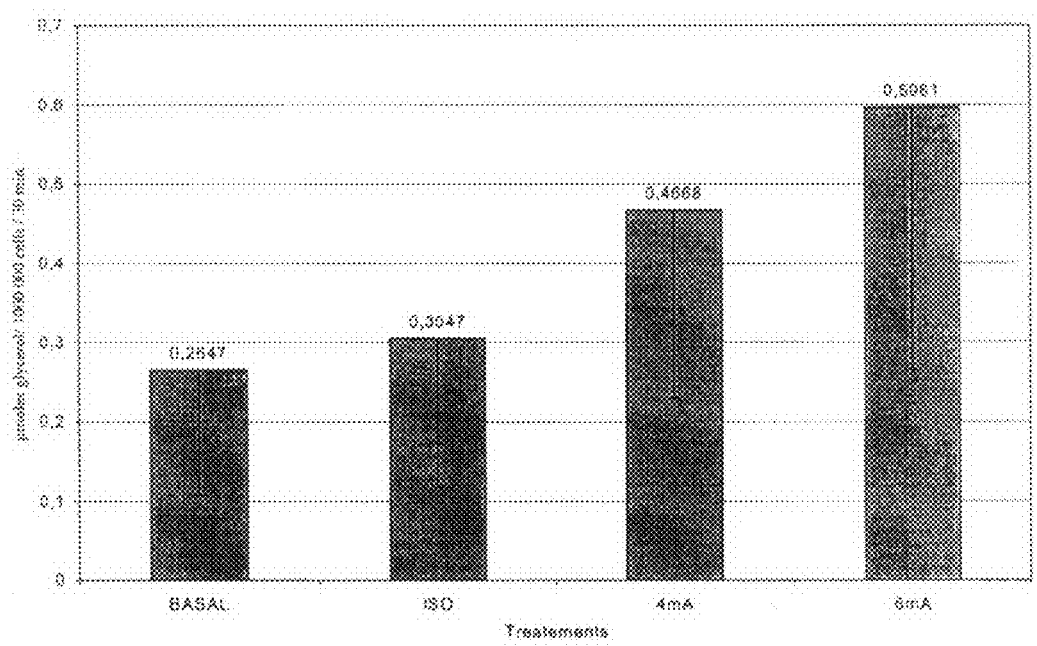
FIG. 3 illustrates the effects of monophasic electrical stimulation on adipocyte lipolysis in humans.

It is disclosed that 2 mA and 6 mA monophasic stimulations increased basal lipolysis by less that 15% (FIG. 3). This level of stimulation appears not significant through repeated T test procedures.

These data confirm that in the case of monophasic stimulations, a current between 2 mA and 6 mA, and preferably 4 mA succeeded significantly to increase adipocyte lipolysis.

EXAMPLE V

Cell Viability Following Electrical Stimulation of Adipocyte

Cell viability was determined using two manners: first through blue trypan dye that consist of counting only cells that were showing their membrane colored by blue trypan while cells with their cytosol colored were considered as non viable; second, cells were stimulated by ISO after they had been electrically stimulated for 30 min. Thus if the electrical stimulation affected the metabolism of the cells their response to ISO would be decreased.

For the monophasic study, the 2 mA and 4 mA stimulation had no effect on the cell count and the ISO stimulation of lipolysis was normal. However, the 6 mA showed a small decrease of cell counts but the ISO stimulation was also normal.

Following biphasic stimulation, the 4 mA and 6 mA stimulations had no effect on the cell count and ISO stimulation of adipocyte lipolysis was normal.

The data support the fact that monophasic stimulations at 2 mA and 4 mA as well as biphasic stimulations at 4 mA and 6 mA do not affect cell viability. Moreover, one must take into account that, in the present study, cells were isolated from human tissue and thus very much more fragile than in situ. It is thus reasonable to consider for a person skilled in the art that the present electrical stimulation (monophasic 2 mA 4 mA; biphasic 4 mA 6 mA) has no effect on the viability of cells if applied in vivo.

EXAMPLE VI

Current Flow Through

In correlation with the present invention, a pre-test of measuring the efficacy of current flowing through the skin was evaluated. Muscular transcutaneous electrical stimulation was conducted. The objective was to evaluate the loss of amplitude of the current flowing through the skin. In addition, measurement of the intensity of the current loss due to resistance of the skin was also evaluated.

A current of 4 mA with a monophasic current of 500 ms was used. No pain was observed on the patient, thus the current is not stimulating the nervous fibres responsible for the pain sensation. It was also observed that an application of a current of 4 mA result in muscular contraction, thus recruitment of motor fibres. Consequently, a person skilled in the art would acknowledge that a great majority of the current flowed through the cutaneous barrier and the adipocytes in order to reach the muscular fibres and to produce a muscular contraction. At least 3.8 mA of the 4 mA was flowed through the skin efficiently. Consequently, 95% of the current stimulation applied flowed through the cutaneous barrier. In addition, the square stimulating wave was not affected since alpha-motomeurons were stimulated. Alpha-motorneurons are depolarize efficiently by square stimulating wave. Observation on the oscilloscope showed that only a mild deformation of the wave was noticed. A small curving of the wave was noticed which is associated to the capacitance of skin.

These data demonstrate that 95% of the current stimulation applied flowed through the cutaneous barrier and that the stimulating wave can be considered as a square wave physiologically.

EXAMPLE VII

In Vivo Microdialysis

In correlation with the present invention, in vivo microdialysis was tested. Microdialysis is a technique that allows stimulating adipose tissue in vivo.

In resume, a probe need to be implanted into adipose tissues that will locate in the interstitial space where an equilibrium will be reached between the interstitial fluid and the physiological solution circulating into the probe. When this equilibrium is reached, the probe can catch molecules released from the cells.

The results are obtained in actual concentrations expressed in micro molar ($\mu M$) of glycerol in order to get valid measurements of lipolysis. Three experimental conditions were tested: (1) BASAL (normal lipolysis activity without any stimulation); (2) 6 mA biphasic current electrical stimulation; (3) 7.6 mA biphasic current electrical stimulation.

The subject used in the present study was a 45 year old woman (weighing 166 pounds and measuring 5 foot 8) and the probe was implanted in the abdominal adipose tissue. The 6 mA biphasic stimulation was applied for 30 min as well as the 7.6 mA biphasic stimulation. It is first important to note that it was observed that the electrical field was crossing the skin wall and was reaching adipose tissue. The obtained results confirm this statement.

Figure 4:
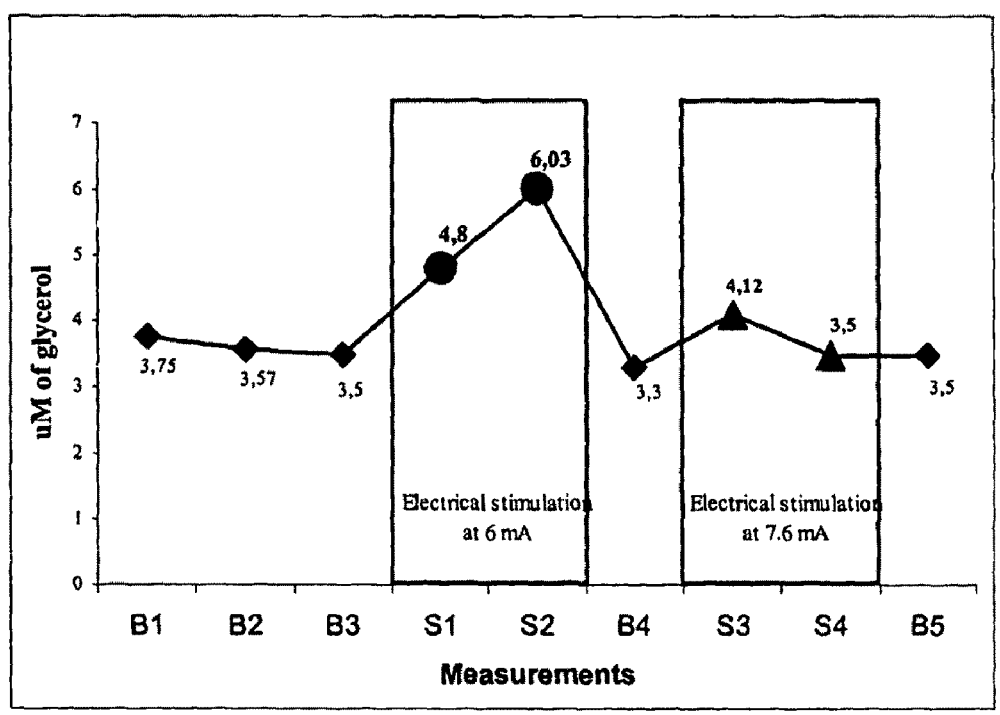
FIG. 4 illustrates a time course of the concentrations of glycerol (measures every 10 min)

Table 2 and FIG. 4 disclose a time course of concentrations of glycerol measured during the experiment (measurements every 10 minutes).

TABLE 2

Time course of concentrations during the experiment (measurements every 10 minutes).

| | BASAL (30 min) | | | 6 mA (20 min) | | Basal (10 min) | 7.6 mA (20 min) | | Basal (10 min) |
|---|---|---|---|---|---|---|---|---|---|
| | B1 | B2 | B3 | S1 | S2 | B4 | S3 | S4 | B5 |
| µM of glycerol | 3.75 | 3.57 | 3.5 | 4.8 | 6.03 | 3.3 | 4.12 | 3.5 | 3.5 |

Figure 5:
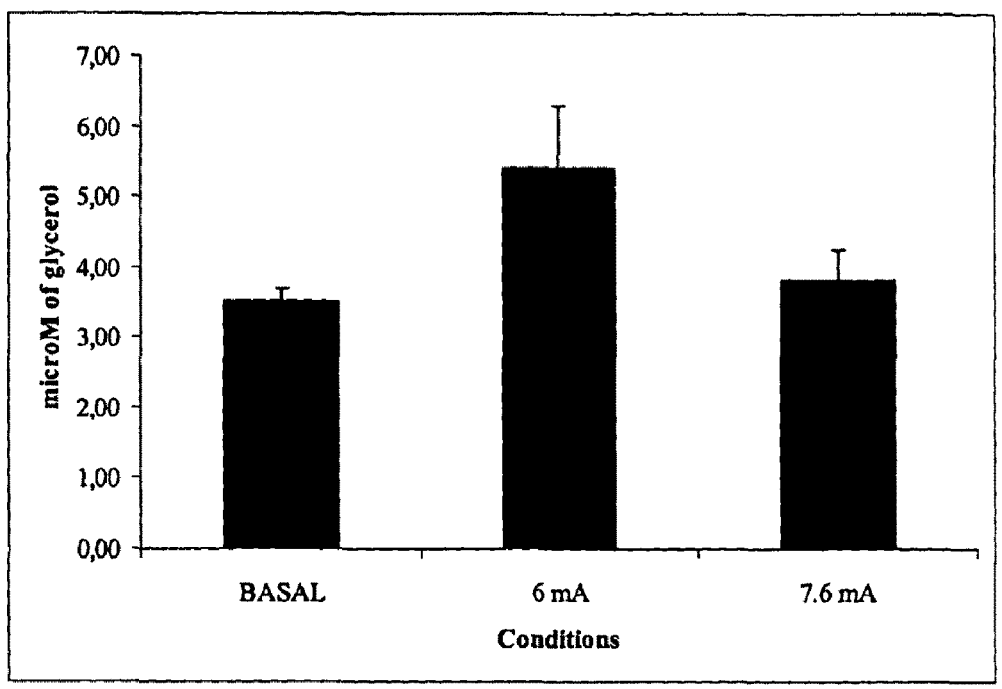
FIG. 5 illustrates an histogram of the means and standard deviations of the concentrations of glycerol.

The results obtained are represented in Table 3 and FIG. 5.

TABLE 3

Summary table presenting the mean concentrations (μ with the standard deviations (S.D.) and percent changes relative to mean baseline concentrations, Concentrations in microM of glycerol

| Conditions | BASAL | 6 mA | 7.6 mA |
|---|---|---|---|
| Means | 3.52 | 5.42 | 3.81 |
| S.D. | 0.16 | 0.87 | 0.44 |
| % change | 100% | 154% | 108% |

Figure 6:
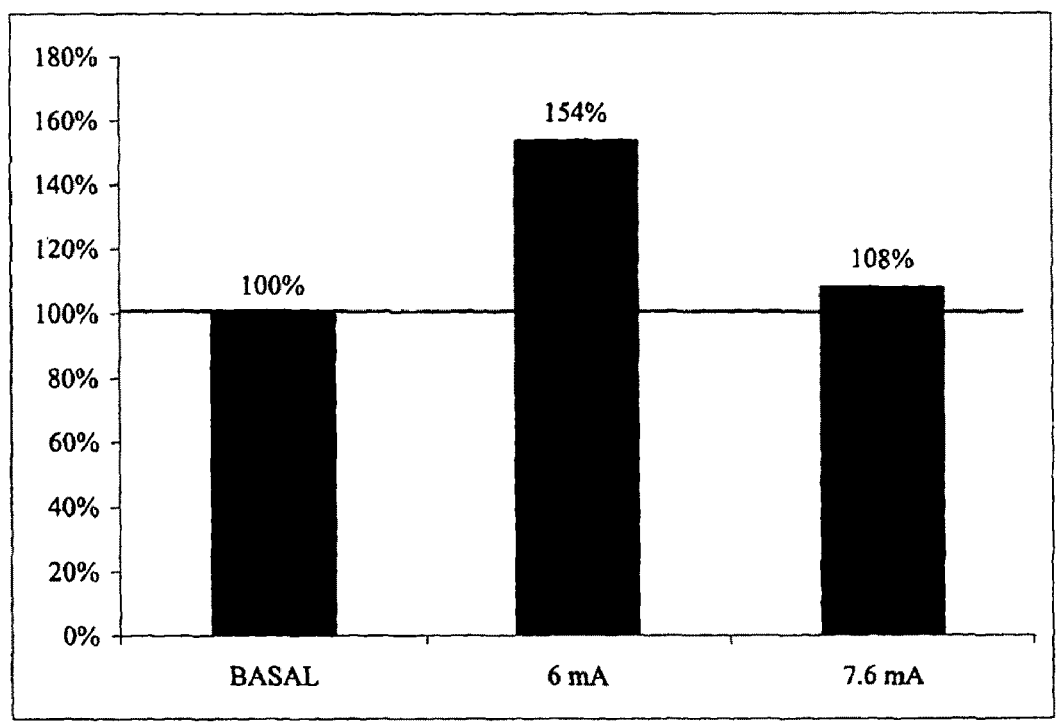
FIG. 6 illustrates an histogram of the percent changes relative to baseline values.

These results demonstrate that 6 mA electrical stimulation produced significantly stimulated lipolysis at a level 54% higher than the normal basal value (FIG. 6). The 7.6 mA electrical stimulation did not produce significant lipolysis. These results, taken in vivo in a human living subject, validate the results found in vitro.

These data demonstrate the correlation between in vitro data obtained and the capacity of the present invention to increase fat cell lipolysis in vivo.

Without wishing to be bound to any specific theory, these results suggest that the electrical current applied to the cells modifies the potential of their membranes, probably by inactivating (e.g. closing) voltage-gated potassium channels. In return, the accumulation of intracellular potassium might activate lipolytic pathways without activating the β-adrenergic receptors.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for increasing lipolysis in a fat cell of a subject, said method comprising applying an electrical current from about 2 mA to about 6 mA to said cell to depolarize the membrane of the cell, wherein said cell remains substantially viable following said application and lipolysis is increased in the depolarized cell.

2. The method of claim 1, wherein said electrical current is biphasic.

3. The method of claim 1, wherein said electrical current is monophasic.

4. The method of claim 1, wherein said electrical current is about 4 mA.

5. The method of claim 1, wherein said depolarization causes an alteration in the activity of an ion channel in said cell.

6. The method of claim 5, wherein said depolarization causes a decrease in the activity of an ion channel in said cell.

7. The method of claim 6, wherein said ion channel is one from an ion channel family selected from the group consisting of EAG, KCNQ, SK, slo, and Kv.

8. The method of claim 7, wherein the ion channel is selected from the group consisting of eag, erg, elk, KCNQ1, KCNQ2, KCNQ3, KCNQ4, KCNQ5, Kv1, Kv2, Kv3, Kv4, Kv5, Kv6, Kv7, Kv8, and Kv9.

9. The method of claim 6, wherein said ion channel is a potassium channel

10. The method of claim 1, wherein said cell is an adipocyte.

11. The method of claim 1, wherein said subject is a mammal.

12. The method of claim 11, wherein said mammal is a human.

13. The method of claim 10, wherein said adipocyte is located in a subcutaneous tissue, a visceral adipose tissue or an intramuscular tissue.

14. The method of claim 13, wherein said subcutaneous tissue is located in a region selected from the group consisting of arm, knee, calf, abdomen, thigh, buttock and hip.

15. The method of claim 1, wherein said increase in lipolysis is at least 1.5 fold with respect to the level of lipolysis in a control cell.

* * * * *